United States Patent [19]
Christensen et al.

[11] Patent Number: 5,571,719
[45] Date of Patent: Nov. 5, 1996

[54] CATALASE, ITS PRODUCTION AND USE

[75] Inventors: Bjørn E. Christensen, Holte; Niels K. Lange, Søborg, both of Denmark; Kosaku Daimon, Funabashi, Japan

[73] Assignee: Novo Nordisk A/S, Bagsvaerd, Denmark

[21] Appl. No.: 117,201

[22] PCT Filed: Mar. 27, 1992

[86] PCT No.: PCT/DK92/00098
§ 371 Date: Sep. 15, 1993
§ 102(e) Date: Sep. 15, 1993

[87] PCT Pub. No.: WO92/17571
PCT Pub. Date: Oct. 15, 1992

[30] Foreign Application Priority Data

Mar. 27, 1991 [EP] European Pat. Off. ............... 91610024
Jun. 4, 1991 [EP] European Pat. Off. ............... 91610050

[51] Int. Cl.$^6$ .................................................. D06M 16/00
[52] U.S. Cl. ............................ 435/264; 134/901; 422/30; 424/94.4; 435/192; 435/254.1; 435/911; 514/839

[58] Field of Search ...................... 435/264, 911, 435/254.1, 192; 514/839; 424/94.4; 134/901; 422/30

[56] References Cited

U.S. PATENT DOCUMENTS 5,273,896  12/1993  Pedersen et al. ...................... 435/192

OTHER PUBLICATIONS

Hudson et al. *Practical Immunology* 2nd Ed. Blackwell Scientific Publications, London, 1980. pp. 8, 117–121.
Weir, D. M. (Ed.) Handbook of Experimental Immunology vol I Immunochemistry 3rd Ed. Blackwell Scientific Publications, London 1978. pp. 14.1, 14.26.

*Primary Examiner*—Leslie Wong
*Attorney, Agent, or Firm*—Steve T. Zelson, Esq.; Elias J. Lambiris, Esq.

[57] ABSTRACT

The present invention relates to catalases obtained from a strain of *Scytalidium thermophilum* or *Humicola insolens* which retains at least 75% residual activity after 20 minutes at 70° C. and a pH in the range of 9.0–10.5 in the presence of 40 mM polyvinyl pyrrolidone and methods for producing and using same.

15 Claims, No Drawings

5,571,719

CATALASE, ITS PRODUCTION AND USE

CROSS-REFERENCE TO RELATED APPLICATIONS

This application is a 35 U.S.C. 371 national application of PCT/DK92/00098 filed Mar. 27, 1992, which is incorporated herein by reference.

TECHNICAL FIELD

This invention relates to a novel catalase preparation, a process for its production and to its use in removal of hydrogen peroxide.

BACKGROUND ART

Catalase (EC 1.11.1.6) is an enzyme that catalyses the decomposition of hydrogen peroxide into water and molecular oxygen. It can be used to remove residual hydrogen peroxide in applications where hydrogen peroxide is added e.g. for pasteurization or bleaching.

Thus, it has been suggested to use catalase in the textile industry for the removal of hydrogen peroxide from fabric which is bleached by an alkaline hydrogen peroxide treatment before dyeing (GB 2,216,149, JP-A 2-104781) The peroxide bleaching is commonly done at high pH and temperature, e.g. 80°–100° C. and pH 10 or higher, and it is therefore desirable to use a catalase with good stability at high pH and temperature in order to avoid or minimize the need for neutralization and cooling.

Catalases are known both from animal sources (e.g. cow liver) and from many different microorganisms. JP-A 2-76579 discloses catalase from *Aspergillus niger* strain NFAG-2 at pH 3–8. GB 2,216,149 states that catalase from Penicillium has good stability at high pH.

It is the object of this invention to provide an improved catalase for use in such processes.

STATEMENT OF THE INVENTION

We have unexpectedly found that a novel catalase can be obtained from strains of Scytalidium and Humicola, two genera not previously reported to produce catalase, and we have further found that, surprisingly, this novel catalase has better stability at high pH and temperature than known catalases.

Accordingly, the invention provides a catalase, characterized by having a pH optimum of approx. 6–8 and immunochemical properties identical to those of catalase produced by a catalase-producing strain of Scytalidium. In another aspect the invention provides a catalase preparation, characterized by being derived from a strain of Scytalidium and by at least 75% residual activity after 20 minutes at 70° C., pH 9–10.5 in the presence of 40 ppm polyvinyl pyrrolidone.

The invention further provides a process for the production of catalase, characterized by comprising cultivation in a suitable nutrient medium of a microorganism containing a gene encoding for and expressing a catalase derived from a strain of the genus Humicola or the genus Scytalidium, preferably followed by recovery of catalase from the culture medium. Finally, the invention provides use of said catalase in removal of hydrogen peroxide.

DETAILED DESCRIPTION OF THE INVENTION

Microorganism

The Humicola-Scytalidium complex is described by D. H. Ellis, Trans. Br. Mycol. Soc. 78 (1), 129–139 (1982). All isolates belonging to this complex can be placed in two distinct species: *Humicola insolens* (Cooney & Emerson) and *Scytalidium thermophilum* (Cooney & Emerson) Austwick.

The definition and taxonomy of the genus Scytalidium is described by Pesante, 1957, Annali Sper. Agr. N.S., 11, Suppl.: CCLXI–CCLXV, and by M. B. Ellis (1971), Dematiaceous Hyphomycetes, Commonwealth Mycological Institute, Kew, Surrey, England, page 28.

Examples of catalase producing strains of *S. thermophilum* are strains ATCC 28085, ATCC 48409 and CBS 671.88, and of *H. insolens* are strains UAMH 2925, IMI 158747 and ATCC 34627, publicly available from American Type Culture Collection, Centralbureau voor Schimmelculturen, University of Alberta Microfungus Collection and Herbaria and CAB International Mycological Institute, respectively.

The Humicola-Scytalidium complex includes the thermophilic hyphomycetes previously classified as *Humicola grisea* var. thermoidea Cooney & Emerson, *H. insolens* Cooney & Emerson and *Torula thermophila* Cooney & Emerson, described in Cooney, D. G. & Emerson, R.: Thermophilic Fungi. An account of their biology, activities and classification. San Fransisco: Freeman (1964).

The strain ATCC 28805 was previously classified as *Torula thermophila*. *Torula thermophila* has now been reclassified as *Scytalidium thermophilum* by Austwick, P.C.K., New Zealand Journal of Agricultural research, 19, 25–33 (1976).

Production of Catalase

Catalase of the invention may be produced by aerobic cultivation of the above microbial strain on a nutrient medium containing suitable carbon and nitrogen sources, such media being known in the art. A temperature in the range 40°–60° C. is suitable for growth and catalase production.

Alternatively, catalase of the invention can be produced by aerobic cultivation of a transformed host organism containing the appropriate genetic information from the above strains. Such transformants can be prepared and cultivated by methods known in the art.

The catalase can be recovered by removing the cells from the fermentation medium (e.g. by filtration) and then concentrating the broth (e.g. by ultrafiltration). If desired, the catalase can be further purified by known methods.

Catalase Preparation

A protease-free catalase preparation is generally preferred for better stability. Some strains used in the invention can produce protease, but a protease-free catalase-producing strain can be obtained by mutation or by transferring the gene encoding catalase into a protease-free transformant by known methods.

The catalase preparation may be in solid or liquid form. A storage-stable liquid preparation can be produced by use of a known stabilizer, e.g. propylene glycol, at pH near neutral.

Immunochemical Properties

Catalase preparations having immunochemical properties identical or partially identical to those of catalase derived from *S. thermophilum* strain ATCC 28085 and having the above-mentioned thermostability are also within the scope of the invention. The immunochemical properties can be determined by immunological cross-reaction identity tests. The identity tests can be performed by the well-known Ouchterlony double immunodiffusion procedure or by tandem crossed immunoelectrophoresis according to N. H. Axelsen; Handbook of Immuno-precipitation-in-Gel Techniques; Blackwell Scientific Publications (1983), chapters 5 and 14. The terms "antigenic identity" and "partial antigenic identity" are described in the same book, chapters 5, 19 and 20.

To elucidate the antigenic identity the Ouchterlony double immunodiffusion procedure, using rabbit antiserum raised against purified *Scytalidium thermophilum* catalase and supernatants from cultures of *S. thermophilum* ATCC 48409 and CBS 671.88 as well as *H. insolens* UAMH 2925, IMI 158747 and ATCC 34627 and a sample of CATAZYME™, a catalase preparation derived from *Aspergillus niger* as well as some pectinase and glucose oxidase, was performed.

The resulting patterns showed complete identity of the catalases produced by the Scytalidium and Humicola strains, and no identity between the Scytalidium catalase and the *A. niger* catalase, as described in Axelsen's book, chapter 5.

Thermostability

The heat stability of the catalase of the invention is better than prior-art enzymes and is almost independent of pH, at least up to pH 10.5. The catalase of the invention can stand temperatures 10° C. higher (at least 70° C.) than prior-art catalase from *A. niger* which is further destabilized by high pH.

The tables below compare the heat stability of the two enzymes. Each enzyme was incubated at the indicated temperature, pH and time in 0.05M phosphate buffer or in 0.18% sodium silicate+0.05% $Na_2CO_3$ (the latter indicated by *), and remaining activity was measured in CIU (described later). 40 ppm polyvinyl pyrrolidone was present in all cases. No $H_2O_2$ was present.

| | 60° C. | | | | | | | |
|---|---|---|---|---|---|---|---|---|
| | Invention | | | | Prior art | | | |
| pH | 9 | 10 | 10* | 10.5 | 9 | 10 | 10* | 10.5 |
| 0 min. | 359 | 383 | 375 | 411 | 401 | 269 | 454 | 303 |
| 20 min. | 420 | 411 | 371 | 411 | 319 | 308 | 308 | 250 |
| 40 min. | 401 | 392 | 348 | 401 | 288 | 288 | 233 | 246 |
| 60 min. | 411 | 401 | 329 | 411 | 245 | 240 | 173 | 209 |

| | 70° C. | | | | | |
|---|---|---|---|---|---|---|
| | Invention | | | Prior art | | |
| pH | 9 | 10 | 10.5 | 9 | 10 | 10.5 |
| 0 min. | 442 | 431 | 431 | 240 | 332 | 493 |
| 20 min. | 371 | 371 | 371 | 70 | 77 | 82 |
| 40 min. | 329 | 303 | 303 | — | — | — |
| 60 min. | 267 | 278 | 246 | — | — | — |

Thus, catalase of the invention, in the pH range 9–10.5, retains at least 90% activity after 60 minutes at 60° C. and at 70° C. at least 75% after 20 min., at least 60% after 40 min. and at least 50% after 60 minutes.

Storage Stability

An aqueous solution of catalase of the invention showed no detectable loss of activity after 4 weeks storage at 37° C., pH 5.5–7.0. A similar experiment with prior-art catalase from *A. niger* showed less than 90% residual activity.

Enzyme Chemical Properties

The catalase of the invention has activity pH optimum at about pH 7 (vs. 5.5 for the prior-art enzyme) and a quite flat pH/activity curve with more than 90% of maximum activity in the range pH 4–9.

The following properties were determined using the purified enzyme of Example 5:

Molecular weight MW=approx. 92,000 (by Pharamaphast SDS)

Iso-electric point pI=approx. 4.5 (by Pharamaphast IEF)

Specific catalase activity of pure enzyme protein=approx. 16,300 CIU/mg protein (CIU see below, protein measured by the Biuret method).

Removal of Hydrogen Peroxide

The catalase of the invention can be used to remove residual hydrogen peroxide in all applications wherein hydrogen peroxide is added for pasteurization, bleaching, smell reduction or other purposes. Examples of such uses are in textile processing, cleaning of contact lenses and treatment of herring roe (as described in JP-A 2-76579).

In the textile industry, catalase can be used to ensure uniform dyeing by removing residual peroxide after its use as a bleaching agent. The process is described in GB 2,216,149 and JP-A 2-104781. Typically, the catalase treatment will take place for 10–30 minutes at 60°–100° C., pH 9–11, particularly 60°–70° C., pH 9–10.5 for 10–60 min. Typically, the initial hydrogen peroxide concentration is 200–2000 ppm and the catalase dosage 3,000–30,000 CIU/l (unit defined below).

In the daily care of contact lenses, these may be disinfected with hydrogen peroxide and then treated with catalase in a physiological saline solution at pH near neutral. The good storage stability makes catalase of the invention well suited for this purpose.

Catalase Determination

One catalase unit CIU will decompose one μmole of $H_2O_2$ per minute at pH 7.0, 25° C., while the $H_2O_2$ concentration decreases from 10.3 to 9.2 μmoles per ml reaction mixture. The degradation of hydrogen peroxide is followed spectrophotometrically at 240 nm.

EXAMPLE 1

Cultivation of *S. thermophilum*

100 ml of a medium containing 30 g/l dextrin, 50 g/l PHARMAMEDIA™, a cottonseed derived protein flour, 0.2 g/l $MgSO_4.7H_2O$, 8 g/l $Na_2HPO_4.12H_2O$, 3 g/l $KH_2PO_4$, 0.1 ml/l PLURONIC™, a polyoxyalkylene ether, was put into a 500 ml Erlenmeyer flask with 2 baffles. The pH was adjusted to 7.0 before sterilization (autoclaving) which was performed at 120° C. for 20 minutes. The sterilized medium was inoculated with small pieces of Bacto Potato Dextrose Agar (Difco) containing sporulating growth of *Scytalidium thermophilum*, ATCC 28085. This culture is allowed to grow at 40° C. for up to 6 days at 250 rpm on an orbital shaker.

EXAMPLE 2

Cultivation of *S. thermophilum*

*Scytalidium thermophilum*, ATCC 28085, was cultured for 4–6 days as in Example 1, and 5 ml of this culture was inoculated into 100 ml medium as in Example 1 and this new culture was grown for 75 hours under similar conditions as in Example 1. The pH after 75 hours was 8.6. The filtrate of this culture had a catalase titre of 10,700 CIU/ml.

EXAMPLE 3

Cultivation of *H. insolens*

100 ml of the medium used in Example 1 was inoculated with small pieces of Bacto Potato Dextrose Agar (Difco) containing profuse growth of *Humicola insolens* IMI 158747. This culture was allowed to grow at 30° C. for up to 3 days at 250 rpm on an orbital shaker. 5 ml of this culture was inoculated into 100 ml medium as in Example 1, and this new culture was grown for 165 hours at 30° C. at 250 rpm on an orbital shaker. The pH after 165 hours was 8.5. The filtrate of this culture had a catalase titre of 3820 CIU/ml.

EXAMPLE 4

Removal of Hydrogen Peroxide at High Temperature and pH

Catalase of the invention was compared with two prior-art enzymes in removal of hydrogen peroxide at 60° C., pH 10.

The culture filtrate of Example 2 was tested together with catalase from *A. niger* prepared according to JP-A 2-76579 and a commercial catalase preparation Ask™ 25 (product of Mitsubishi Gas Chemical).

The reaction conditions were 60° C., pH 10 (0.4 g $NaHCO_3$ + 0.6 g $Na_2CO_3$ per liter), 25–1500 ppm $H_2O_2$ (as indicated below) and enzyme concentration 2000–30000 CIU/l (as indicated below).

Residual $H_2O_2$ was detected by Merck Peroxide Test Paper. This was done at time 10, 15 and 20 min. after enzyme addition to the $H_2O_2$ solution.

The results are shown in the tables below where the following symbols are used:

| | |
|---|---|
| ⊙ | $H_2O_2$ was removed within 10 min. |
| ○ | $H_2O_2$ was removed within 15 min. |
| △ | $H_2O_2$ was removed within 20 min. |
| — | $H_2O_2$ was not removed within 20 min. |
| A | Catalase dosage (CIU/liter) |
| B | $H_2O_2$ (ppm) |

Catalase of the invention

| | A | | | | | | | | | |
|---|---|---|---|---|---|---|---|---|---|---|
| B | 30000 | 22500 | 20000 | 15000 | 10000 | 7500 | 6000 | 3750 | 3000 | 2000 |
| 1500 | ⊙ | ⊙ | ○ | ○ | — | — | — | — | — | — |
| 1000 | ⊙ | ⊙ | ⊙ | ⊙ | — | — | — | — | — | — |
| 750 | ⊙ | ⊙ | ⊙ | ⊙ | ○ | — | — | — | — | — |
| 500 | ⊙ | ⊙ | ⊙ | ⊙ | ⊙ | △ | — | — | — | — |
| 250 | ⊙ | ⊙ | ⊙ | ⊙ | ⊙ | ⊙ | ○ | △ | — | — |
| 100 | ⊙ | ⊙ | ⊙ | ⊙ | ⊙ | ⊙ | ⊙ | ○ | — | — |
| 75 | ⊙ | ⊙ | ⊙ | ⊙ | ⊙ | ⊙ | ⊙ | ○ | — | — |
| 50 | ⊙ | ⊙ | ⊙ | ⊙ | ⊙ | ⊙ | ⊙ | ○ | △ | — |
| 25 | ⊙ | ⊙ | ⊙ | ⊙ | ⊙ | ⊙ | ⊙ | ⊙ | ○ | — |

Catalase from *A. niger* (reference)

| | A | | | | | | | | | |
|---|---|---|---|---|---|---|---|---|---|---|
| B | 30000 | 22500 | 20000 | 15000 | 10000 | 7500 | 6000 | 3750 | 3000 | 2000 |
| 1500 | ⊙ | ⊙ | — | — | — | — | — | — | — | — |
| 1000 | ⊙ | ⊙ | ○ | — | — | — | — | — | — | — |
| 750 | ⊙ | ⊙ | ⊙ | △ | — | — | — | — | — | — |
| 500 | ⊙ | ⊙ | ⊙ | ⊙ | — | — | — | — | — | — |
| 250 | ⊙ | ⊙ | ⊙ | ⊙ | △ | △ | — | — | — | — |
| 100 | ⊙ | ⊙ | ⊙ | ⊙ | △ | △ | — | — | — | — |
| 75 | ⊙ | ⊙ | ⊙ | ⊙ | ⊙ | △ | — | — | — | — |
| 50 | ⊙ | ⊙ | ⊙ | ⊙ | ⊙ | ○ | — | — | — | — |
| 25 | ⊙ | ⊙ | ⊙ | ⊙ | ⊙ | ⊙ | ○ | — | — | — |

Ask 25, (reference)

| | A | | | | | | | | | |
|---|---|---|---|---|---|---|---|---|---|---|
| B | 30000 | 22500 | 20000 | 15000 | 10000 | 7500 | 6000 | 3750 | 3000 | 2000 |
| 1500 | — | — | — | — | — | — | — | — | — | — |
| 1000 | — | — | — | — | — | — | — | — | — | — |
| 750 | — | — | — | — | — | — | — | — | — | — |
| 500 | — | — | — | — | — | — | — | — | — | — |
| 250 | — | — | — | — | — | — | — | — | — | — |
| 100 | — | — | — | — | — | — | — | — | — | — |
| 75 | — | — | — | — | — | — | — | — | — | — |
| 50 | — | — | — | — | — | — | — | — | — | — |
| 25 | — | — | — | — | — | — | — | — | — | — |

The results clearly demonstrate that catalase of the invention is superior to the prior-art enzymes for removal of $H_2O_2$ at high temperature and pH. Thus, CIU/L of catalase of this invention could remove 25–100 ppm hydrogen peroxide within 10 minutes.

EXAMPLE 5

Removal of $H_2O_2$ at 60° C.

The experiment was performed at 60° C. in an 0.05M phosphate buffer pH 9 or 10 (as indicated below) containing 1000 ppm $H_2O_2$. 10 CIU/ml of catalase of the invention (culture filtrate of Example 2) was added, and the amount of $H_2O_2$ was measured after 20, 40 and 60 minutes. Results (ppm $H_2O_2$):

| | pH 9 | pH 10 |
|---|---|---|
| 20 min. | 8 | 11 |
| 40 min. | 5 | 7 |
| 60 min. | 5 | 6 |
| Blank (no enzyme): | | |
| 60 min. | >900 | 850 |

These data demonstrate reduction to a very low level of $H_2O_2$ at these conditions, where Example 4 showed incomplete removal in 20 min. at pH 10.

EXAMPLE 6

Purification of Catalase

42% w/w ethanol was added to culture filtrate prepared as in Example 1 to precipitate the catalase. After centrifugation the precipitate was redissolved in ion exchanged water to the original volume.

pH was adjusted to 4.5 and the redissolved catalase was treated with 3% w/w bentonite (Clarite BW) and 3% w/w active carbon (Picatif FGV) (room temperature, 1 hour stirring). Bentonite and active carbon were removed by centrifugation followed by a sterile filtration.

pH was adjusted to 5.0 and the filtrate was treated in a batch process with CM-Sepharose (Pharmacia) over-night at 4° C. (1 ml CM-Sepharose per 200,000 CIU). The ion exchange resin was washed with 10 volumes 0.025M phosphate buffer+0.09M NaCl at pH 5.0.

The final purification step was performed on a chromatofocusing resin PBE 94 from Pharmacia: The buffer was changed by dialysis to a 0,025 piperazine/HCl buffer at pH 5.5, and the catalase was then absorbed on a PBE 94 column and eluted with POLYBUFFER 74 HCl, a mixture of synthetic poly-electrolytes, at pH 4.0 followed by 1M NaCl solution. The catalase was found in the 1M NaCl solution.

We claim:

1. An isolated catalase obtained from a strain of *Scytalidium thermophilum* or *Humicola insolens* which retains at least 75% residual activity after 20 minutes at 70° C. and a pH the range of 9.0–10.5 in the presence of 40 mM polyvinyl pyrrolidone.

2. A catalase according to claim 1 which is obtained from a strain of *Scytalidium thermophilum*.

3. A catalase according to claim 2, wherein the strain is *S. thermophilium* ATCC 28085, *S. thermophilum* ATCC 48409, or *S. thermophilum* CBS 671.88.

4. A catalase according to claim 1 which is obtained from a strain of *Humicola insolens*.

5. A catalase according to claim 4, wherein the strain is *H. insolens* IMI 158747 or *H. insolens* ATCC 34627.

6. A catalase preparation comprising a catalase according to claim 1 and a stabilizer.

7. A catalase preparation according to claim 6 which is obtained from a strain of *S. thermophilum*.

8. A catalase preparation according to claim 7, wherein the strain is *S. thermophilum* ATCC 28085, *S. thermophilum* ATCC 48409, or *S. thermophilum* CBS 671.88.

9. A catalase preparation according to claim 6 which is obtained from a strain of *H. insolens*.

10. A catalase preparation according to claim 9, wherein the strain is *H. insolens* IMI 158747 or *H. insolens* ATCC 34627.

11. A process for producing a catalase according to claim 1, comprising
   (a) cultivating a catalase-producing strain of *Scytalidium thermophilum* or *Humicola insolens* in a nutrient medium under conditions conducive to catalase production; and;
   (b) recovering the catalase from the culture.

12. A process according to claim 11, wherein the strain is *S. thermophilum* ATCC 28085, ATCC 48409 or CBS 671.88 or *H. insolens* IMI 158747 or ATCC 34627, or a mutant or variant thereof which possesses the parent's ability to produce the catalase.

13. A process according to claim 11, wherein the cultivation is performed at a temperature in the range of 40°–60° C., 14. A method for cleaning contact lenses comprising
   (a) treating the contact lenses with hydrogen peroxide, and
   (b) treating the hydrogen peroxide-treated contact lenses with a catalase according to claim 1 for a time sufficient to remove the hydrogen peroxide.

15. A method for cleaning contact lenses comprising
   (a) treating the contact lenses with hydrogen peroxide, and
   (b) treating the hydrogen peroxide-treated contact lenses with a catalase preparation according to claim 6 for a time sufficient to remove the hydrogen peroxide.

* * * * *